United States Patent [19]

Doehner, Jr.

[11] Patent Number: 4,925,944

[45] Date of Patent: May 15, 1990

[54] PROCESS FOR THE PREPARATION OF O-CARBOXYPYRIDYL- AND O-CARBOXYQUINOLYLIMIDAZOLI-NONES

[75] Inventor: Robert F. Doehner, Jr., East Windsor, N.J.

[73] Assignee: American Cyanamid Company, Stamford, Conn.

[21] Appl. No.: 326,846

[22] Filed: Mar. 21, 1989

[51] Int. Cl.$^5$ .......................................... C07D 401/04
[52] U.S. Cl. .................................. 546/167; 546/168; 546/169; 546/278
[58] Field of Search ................ 548/278; 546/168, 169, 546/167

[56] References Cited

U.S. PATENT DOCUMENTS

| 4,474,962 | 10/1984 | Wepplo | 546/167 |
| 4,638,068 | 1/1989 | Los | 546/169 |
| 4,656,283 | 4/1987 | Doehner, Jr. | 546/178 |
| 4,723,011 | 2/1988 | Doehner, Jr. | 546/250 |
| 4,798,619 | 1/1989 | Los | 71/66 |

*Primary Examiner*—David B. Springer
*Attorney, Agent, or Firm*—John W. Hogan, Jr.

[57] ABSTRACT

The present invention provides an improved process for the preparation of o-carboxypyridyl- and o-carboxyquinolylimidazolinones from their 2-methyl-o-carboxylate pyridine and quinoline precursors.

11 Claims, No Drawings

PROCESS FOR THE PREPARATION OF O-CARBOXYPYRIDYL- AND O-CARBOXYQUINOLYLIMIDAZOLINONES

BACKGROUND OF THE INVENTION

The invention herein described relates to a process for the preparation of herbicidal agents. More specifically it relates to an improved process for the preparation of certain o-carboxypyridylimidazolinones and o-carboxyquinolylimidazolinones.

Because the o-carboxypyridinyl- and o-carboxyquinolylimidazolinones of the present invention are excellent herbicidal agents, there is an ongoing search in the art for new and improved methods of preparing them. Unfortunately, the processes known in the art generally require excess starting material (e.g. the 2-quinaldine or 2-picoline precursor) or produce less than favorable yields or both. Additionally, in order to produce the desired end product some processes require many separate steps or require that less direct methods or circuitous routes be taken so that poor yields are avoided.

U.S. Pat. No. 4,474,962 describes a process for the condensation of substituted 2-picolines or 2-quinaldines with an aminocarboxamide and sulfur to form substituted 2-imidazolinylpyridines or 2-imidazlinylquinolines, respectively. However, this process requires the use of excess amounts of the 2-picoline or 2-quinaldine precursor to obtain goods yields of the corresponding 2-imidazolinylpyridine or quinoline product. In addition the best yields are obtained when the substituent in the 3 position of the 2-picoline or 2-quinaldine precursor is a hydrogen, thereby requiring the desired o-carboxylate functionality to be added in a separate sequential metallation/carboxylation step.

Commercially, the elimination of (1) excess starting material, (2) extra metallation/carboxylation steps and (3) low product yield would be significantly advantageous.

It is an object of this invention to provide a dramatic improvement in the process for the preparation of o-carboxypyridyl- and o-carboxyquinolylimidazolinones via a single step reaction which eliminates unnecessary extra steps and produces compounds of formula I in significantly increased yields while simultaneously reducing the use of excess amounts of reactants.

SUMMARY OF THE INVENTION

The present invention relates to an improved process for the preparation of o-carboxypyridylimidazolinones and o-carboxyquinolylimidazolinones of formula I via a single step condensation of the appropriately substituted 2-methylpyridine and 2-methylquinoline o-carboxylate precursors of formula II with aminoamides of formula III in the presence of sulfur and an aromatic solvent at a temperature range of about 100° C.–200° C. as shown in the following scheme:

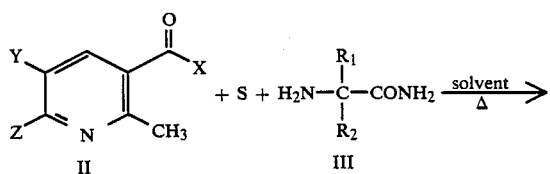

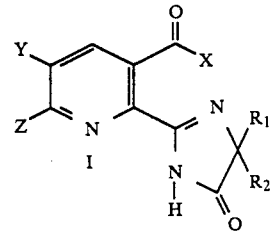

wherein

X is $OR_3$ or $NR_4R_5$;

Y is hydrogen, halogen, or $C_1$–$C_6$ alkyl optionally substituted by one or two $C_1$–$C_4$ alkoxy groups;

Z is hydrogen; and when taken together with the carbons to which they are attached Y and Z may form a ring in which YZ is —CH=CH—CH=CH—;

$R_1$ and $R_2$ are $C_1$–$C_4$ alkyl or when taken together they may represent $C_3$–$C_6$ cycloalkyl optionally substituted with methyl and when $R_1$ and $R_2$ are not the same, the optical isomers thereof;

$R_3$ is $C_1$–$C_6$ alkyl, $C_5$–$C_6$ cycloalkyl or benzyl optionally substituted by one or two $C_1$–$C_6$ alkyl, $C_1$–$C_4$ alkoxyl, or halo;

$R_4$ and $R_4$ are $C_1$–$C_4$ alkyl, or when taken together with the nitrogen to which they are attached, they may represent piperidinyl or morpholinyl.

It has now been found that a single step condensation reaction to produce compounds of formula I is significantly improved by conducting the reaction in the presence of an aromatic solvent and in the presence of at least a 2-fold excess of sulfur at a temperature range of about 100° C.–200° C., thereby requiring only about one equivalent of a compound of formula II and about one equivalent of a compound of formula III.

Surprisingly, it has been found that the use of an aromatic solvent such as toluene, xylene, naphthalene, chlorobenzene, dichlorobenzene, chlorotoluene and the like, in amounts of about 50–300 wt%, based on the weight of the compound of formula II and the use of about 5.5–9.0 molar equivalents of sulfur present at a temperature range of about 100° C.–200° C. gives a highly efficient and greatly improved method for the preparation of compounds of formula I in significantly increased yield.

DESCRIPTION OF THE PREFERRED EMBODIMENTS

The invention relates to an improved method for the preparation of substituted and unsubstituted o-carboxypyridyl- and o-carboxyquinolylimidazolinones of formula I via a single step condensation reaction of one equivalent of the appropriately substituted 2-methylpyridine or 2-methylquinoline carboxylate precursor of formula II with one equivalent of aminoamides of formula III in the presence of 5.5–9.0, preferably about 6.0, molar equivalents of sulfur and in the presence of about 50–300 wt%, preferably about 75–125 wt%, (based on the weight of the formula II compound) of an aromatic solvent at a temperature range of about 100° C.–200° C., preferably about 130° C.–170° C., as illustrated in the following scheme:

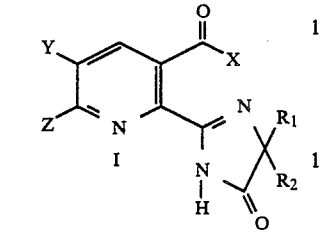

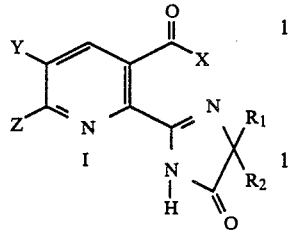

wherein
X is OR$_3$ or NR$_4$R$_5$;
Y is hydrogen, halogen, or C$_1$-C$_6$ alkyl optionally substituted by one or two C$_1$-C$_4$ alkoxy groups;
Z is hydrogen; and when Y and Z are taken together with the carbons to which they are attached, Y and Z may form a ring in which YZ is —CH=CH—CH=CH—;
R$_1$ and R$_2$ are C$_1$-C$_4$ alkyl or when taken together they may represent C$_3$-C$_6$ cycloalkyl optionally substituted with methyl and when R$_1$ and R$_2$ are not the same, the optical isomers thereof;
R$_3$ is C$_1$-C$_6$ alkyl, C$_5$-C$_6$ cycloalkyl or benzyl optionally substituted by one or two C$_1$-C$_6$ alkyl, C$_1$-C$_4$ alkoxy or halo;
R$_4$ and R$_5$ are C$_1$-C$_4$ alkyl, or when taken together with the nitrogen to which they are attached, they may represent piperidinyl or morpholinyl.

Aromatic hydrocarbon solvents suitable for use in the method of invention include chlorobenzene, dichlorobenzene, chlorotoluene, toluene, xylene, naphthalene and the like. The preferred solvent is chlorobenzene.

Surprisingly, it has been found that when an aromatic solvent, such as chlorobenzene, is present at about 50-300 wt%, preferably about 75-125 wt%, (based on the weight of the formula II compound) and when about 5.5-9.0 molar equivalents, preferably about 6.0 molar equivalents, of sulfur are present, only one equivalent of 2-methyl-o-carboxypyridine and -quinoline compounds of formula II and one equivalent of aminoamides of formula III are required at temperatures of about 100° C.-200° C., preferably about 130° C.-170° C., to produce compounds of formula I in significantly increased yields.

The present method provides that a stirred mixture of one equivalent of a formula II compound, one equivalent of a formula III compound, about 5.5-9.0 molar equivalents, preferably about 6.0 molar equivalents, of sulfur and about 50-300 wt%, preferably about 75-125 wt%, (based on the formula II compound) of chlorobenzene be heated at about 100° C.-200° C., preferably about 130° C.-170° C., for about 1 to 72 hours. After cooling to room temperature, the reaction mixture is diluted with an organic solvent such as methylene chloride or ether or the like and filtered to remove unreacted sulfur. The filtrate is worked up using conventional isolation methods, such as chromatography, to afford the formula I product in excellent yield.

In order to facilitate a further understanding of the invention, the following examples are presented primarily for the purpose of illustrating more specific details thereof. The invention is not to be limited thereby except as defined in the claims. Unless otherwise noted, all parts are by weight.

EXAMPLE 1

Preparation of Ethyl 5-ethyl-2-methylnicotinate

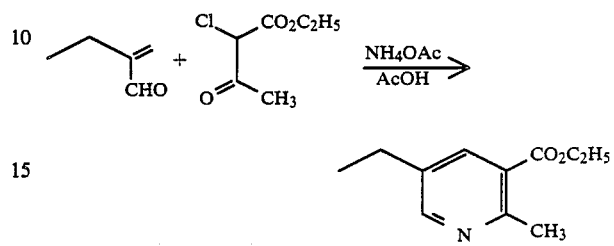

A suspension of 2 kg of ammonium acetate (26 moles) in 4.5 L of acetic acid is mechanically stirred in a 12 L 4-necked flask equipped with a condenser, and treated with 1 kg of 2-ethylacrolein (11.9 moles) in a single portion followed by 2 kg of ethyl 2-chloroacetoacetate (12.1 moles). An exotherm ensues over a period of 5 minutes to the boiling point of the solvent; this condition is maintained (under control) with air cooling for 10 minutes. After stirring overnight at ambient temperatures, the reaction mixture is filtered, the filtrate is concentrated in vacuo, and the residue is partitioned between 2:1 hexane-ethyl acetate and water. The organic phase is washed with water, then extracted thoroughly with 5% aqueous HCl. The combined aqueous extracts are washed with 2:1 hexane-ethyl acetate, made basic with concentrated NH$_2$OH, and extracted with 2:1 hexane-ethyl acetate. The combined organic extracts are dried and concentrated in vacuo, to give an oil residue which is vacuum distilled to afford 1.4 kg of the title product, bp 90°/0.05 mm.

By substituting the appropriate starting materials and performing the analogous reaction sequence, the following compounds are prepared and shown in Table I below.

TABLE I

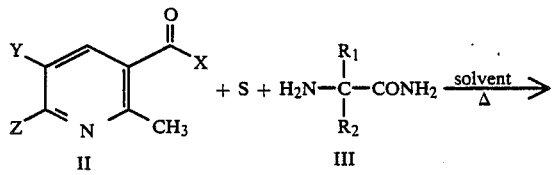

| X | Y | Z | bp |
|---|---|---|---|
| O-cyclohexyl | C$_2$H$_5$ | H | 141°/0.7 mm |
| OCH$_2$-phenyl | C$_2$H$_5$ | H | 161°/0.65 mm |
| OCH(C$_2$H$_5$)$_2$ | C$_2$H$_5$ | H | 115°/0.6 mm |
| OCH$_2$CH(CH$_3$)$_2$ | C$_2$H$_5$ | H | 110°/0.5 mm |
| OCH(CH$_3$)C$_2$H$_5$ | C$_2$H$_5$ | H | 109°/0.6 mm |
| OCH$_2$CH$_2$CH$_2$CH$_3$ | C$_2$H$_5$ | H | 123°/0.65 mm |
| OCH$_2$CH$_2$CH$_3$ | C$_2$H$_5$ | H | 115°/0.55 mm |
| OCH(CH$_3$)$_2$ | C$_2$H$_5$ | H | 82°/0.06 mm |
| OC(CH$_3$)$_3$ | C$_2$H$_5$ | H | 98°/0.15 mm |
| OCH$_3$ | C$_2$H$_5$ | H | 87°/0.4 mm |

TABLE I-continued

Y‐(pyridine with CH₃ at 2-position)‐C(=O)‐X structure

| X | Y | Z | bp |
|---|---|---|----|
| OC₂H₅ | CH₃ | H | 99°/0.6 mm |
| OC₂H₅ | Br | H | 95–105°/0.5 mm |
| OCH₂–C₆H₄–OCH₃ | CH₃ | H | — |

EXAMPLE 2

Preparation of 5-Ethyl-2-methylnicotinic acid

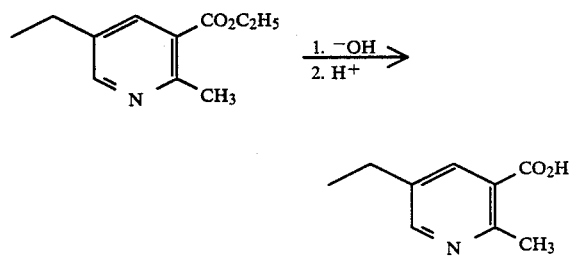

A solution of 260 g of ethyl 5-ethyl-2-methylnicotinate 81.34 mol) in 250 mL methanol is treated in 1 portion with a solution of 80 g of sodium hydroxide (2 mol) in 1 L water. The reaction is stirred at room temperature for 2 days, then concentrated in vacuo to a volume of about 700 mL, and acidified with 167 mL of concentrated hydrochloric acid (2 moles). The precipitated solid is filtered, washed with cold water, and dried in vacuo at 75° C. to afford 184 g of the title product, mp 218°–220° C.

By substituting the appropriate starting ester and performing the analogous reaction sequence, the following compounds are prepared and shown in Table II below.

TABLE II

| Y | Z | mp |
|---|---|----|
| CH₃ | H | 180–184° |
| H | H | 225–227° |

EXAMPLE 3

Preparation of 5-Ethyl-2-methylnicotinic acid, morpholine amide

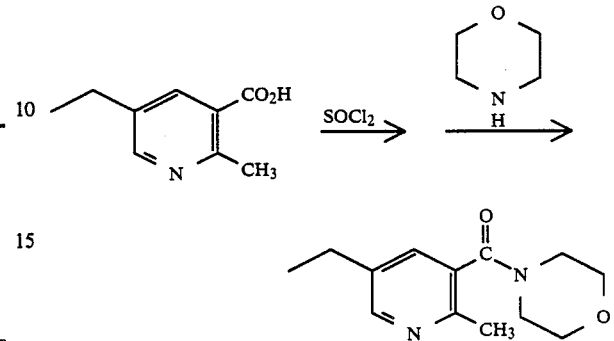

A suspension of 25 g of 5-ethyl-2-methylnicotinic acid (0.15 mol) in 400 mL of methylene chloride containing 10 drops of dimethylformamide is treated in one portion with 50 mL of thionyl chloride. The reaction is stirred under a condenser at room temperature for 20 minutes, then at reflux temperature for 2 hours. The reaction is concentrated in vacuo and reconcentrated from dry toluene to afford the acid chloride hydrochloride intermediate as a solid.

To a suspension of this intermediate in 300 mL of toluene is added 43.5 g of morpholine (0.50 mol) in one portion. The reaction is stirred at room temperature for 1 hour, then partitioned between ethyl acetate and water. The aqueous layer is further extracted with ethyl acetate; the combined organic phase is dried, concentrated in vacuo, and distilled to afford 23 g of the title product, bp 165°/0.75 mm.

By substituting the appropriate starting materials and performing the analogous reaction sequence, the following compounds are prepared and shown in Table III below.

TABLE III

| X | Y | Z | bp |
|---|---|---|----|
| N(C₂H₅)₂ | C₂H₅ | H | oil |
| OCH(CH₃)₂ | H | H | 75°/0.75 mm |
| OCH(CH₃)C₂H₅ | H | H | 100°/0.70 mm |

EXAMPLE 4

Preparation of Ethyl 2-methylquinoline-3-carboxylate

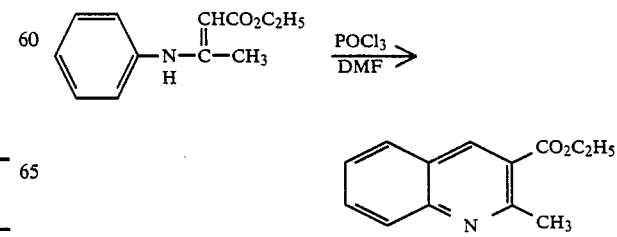

A solution of 140 g of dimethylformamide (1.92 mole) in 500 mL of methylene chloride is mechanically stirred under a condenser/scrubber in an ice bath while 295 g of POCl₃ (1.92 mol) is added dropwise over a 40 minute period. The reaction is stirred for a further 3 hour period, during which time the bath temperature is allowed to warm to room temperature. The reaction is then diluted with 2 L of methylene chloride, cooled in an ice bath, and treated dropwise with 394 g of ethyl β-anilinocrotonate (1.92 mol) over a 1 hour period. After stirring at room temperature for 26 hours, the reaction is heated at reflux temperature for 48 hours, cooled in an ice bath, quenched with 500 mL ice water, and treated portionwise with concentrated NH₄OH to pH 6. The phases are separated and the organic phase is concentrated in vacuo to give a solid residue which is redissolved in 1.5 L ethyl acetate, filtered, and the filtrate saturated with gaseous hydrogen chloride. The resultant solid precipitate is filtered off, washed thoroughly with ethyl acetate, dissolved in water and basified with concentrated NH₄OH. The basic aqueous mixture is extracted with 1:1 hexanes-ethyl acetate; the organic phase is concentrated in vacuo to afford 240 g of the title product, mp 70°-72° C.

By substituting the appropriate starting material and performing the analogous sequence, one can prepare the following:

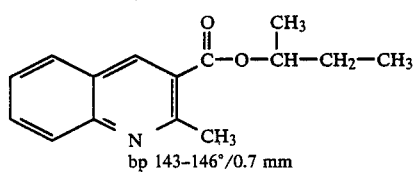

bp 143-146°/0.7 mm

EXAMPLE 5

Preparation of sec-Butyl 5-ethyl-2-(4-isopropyl-4-methyl-5-oxo-2-imidazolin-2-yl)nicotinate

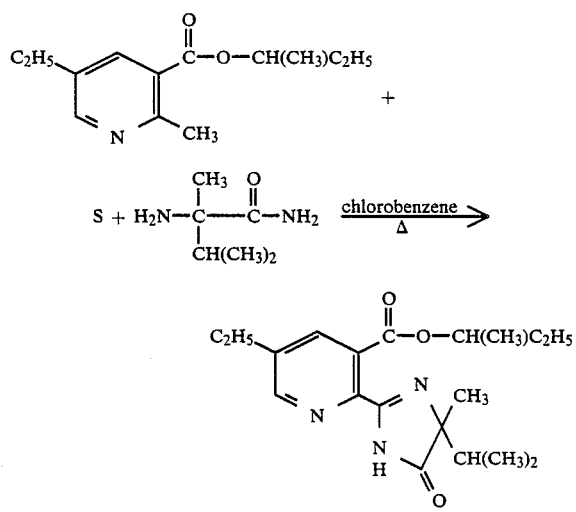

A mixture of 2.2 g of sec-butyl 5-ethyl-2-methyl-nicotinate (10 mmol), 1.3 g of a-methylvalinamide (10 mmol) and 2.0 g of sulfur (62 mmol) in 2.5 g of chlorobenzene (114 wt%) is magnetically stirred at reflux temperatures for 24 hours. The reaction is cooled, diluted with methylene chloride, and filtered to remove unreacted sulfur. The filtrate is chromatographed on silica gel using 2:1 hexane-ethyl acetate as eluant to afford 2.5 g of the title product (72% yield) as a solid; recrystallization from ether-hexane gives mp 83°-87° C.

Using essentially the same procedure, and substituting the appropriate starting material, the following yields are obtained and shown on Table IV below.

TABLE IV

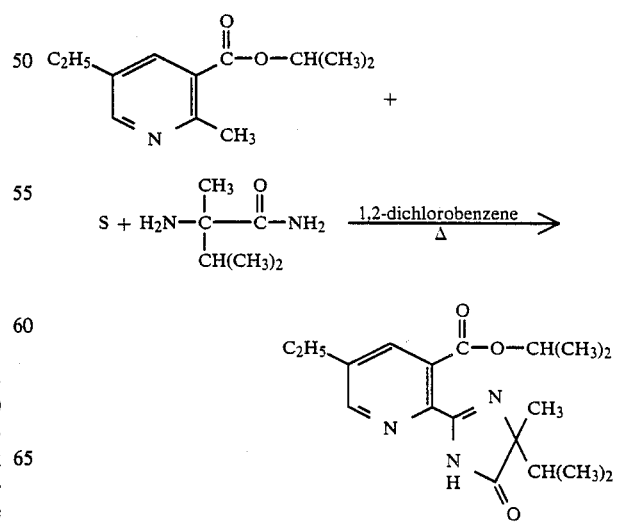

| X | Y | Z | % yield |
|---|---|---|---|
| OCH(CH₃)₂ | C₂H₅ | H | 72 |
| OCH(CH₃)₂ | H | H | 66 |
| OC₂H₅ | —CH=CH—CH=CH— | | 59 |
| OC₂H₅ | C₂H₅ | H | 63 |
| OC₂H₅ | CH₃ | H | 60 |
| OC₂H₅ | H | H | 60 |
| O(CH₂)₃CH₃ | C₂H₅ | H | 65 |
| O-cyclohexyl | C₂H₅ | H | 70 |

EXAMPLE 6

Preparation of Isopropyl 5-ethyl-2-(4-isopropyl-4-methyl-5-oxo-2-imidazolin-2-yl)nicotinate A mixture of 4.2 g of isopropyl 5-ethyl-2-methylnicotinate (20 mmol), 2.7 g of α-methylvalinamide (20 mmol) and 2.0 g sulfur (62 mmol) in 8 mL of 1,2-dichlorobenzene is heated at 160° C. for 19 hours. The reaction mixture is cooled, diluted with methylene chloride, and filtered. The filtrate is chromatographed on silica gel using hexanes, followed by 2:1 hexane-ethyl acetate to afford 5.0 g of crude product. Purity is 51% (38% yield) by NMR spectral analysis.

I claim:

1. A method for the preparation of o-carboxypyridiyl- and o-carboxyquinolylimidazolinones of formula I

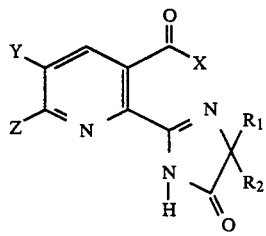

wherein

X is $OR_3$ and or $NR_4R_5$;

Y is hydrogen, halogen, or $C_1$-$C_6$ alkyl optionally substituted by one or two $C_1$-$C_4$ alkoxy groups;

Z is hydrogen; and when Y and Z are taken together with the carbons to which they are attached, they may form a ring in which YZ is —CH=CH—CH=CH—;

$R_1$ and $R_2$ are $C_1$-$C_4$ alkyl or when taken together they may represent $C_3$-$C_6$ cycloalkyl optionally substituted with methyl and when $R_1$ and $R_2$ are not the same, the optical isomers thereof;

$R_3$ is $C_1$-$C_6$ alkyl, $C_5$-$C_6$ cycloalkyl or benzyl optionally substituted by one or two $C_1$-$C_6$ alkyl, $C_1$-$C_4$ alkoxy, or halo;

$R_4$ and $R_5$ are $C_1$-$C_4$ alkyl, or when taken together with the nitrogen to which they are attached, they may represent piperidinyl or morpholinyl;

comprising reacting a compound of formula II

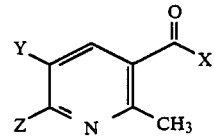

wherein X, Y and Z are as described hereinabove for formula I; with one equivalent of a compound of formula III

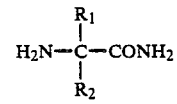

wherein $R_1$ and $R_2$ are as described above for formula I; in the presence of about 50–300 weight%, based on the weight of the compound of formula II, of an aromatic solvent and in the presence of about 5.5–9.0 molar equivalents of sulfur at a temperature range of about 100° C. to 200° C.

2. A method according to claim 1 wherein the aromatic solvent is chlorobenzene, dichlorobenzene, chlorotoluene, toluene, xylene or naphthalene.

3. A method according to claim 2 wherein the solvent is present at about 75–125 weight% based on the weight of the compound of formula II.

4. A method according to claim 3 wherein the solvent is chlorobenzene.

5. A method according to claim 4 wherein the sulfur is present in the amount of about 6.0 molar equivalents.

6. A method according to claim 1 wherein the temperature range is about 130° C. to 170° C.

7. A method according to claim 6 wherein the sulfur is present in the amount of about 6.0 molar equivalents and the solvent is chlorobenzene.

8. A method according to claim 1 wherein Y and Z are hydrogen.

9. A method according to claim 1 wherein Y is methyl and Z is hydrogen.

10. A method according to claim 1 wherein Y is ethyl and Z is hydrogen.

11. A method according to claim 1 wherein Y and Z taken together represent —CH=CH—CH=CH—.

* * * * *